United States Patent
Gau et al.

(10) Patent No.: US 7,514,048 B2
(45) Date of Patent: Apr. 7, 2009

(54) CONTROLLED ODOR GENERATOR

(75) Inventors: Tien-Ho Gau, Hsinchu (TW); Yu-Yin Peng, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 283 days.

(21) Appl. No.: 10/226,970

(22) Filed: Aug. 22, 2002

(65) Prior Publication Data

US 2004/0037764 A1 Feb. 26, 2004

(51) Int. Cl.
- A61L 9/00 (2006.01)
- A62B 7/08 (2006.01)
- B01D 11/04 (2006.01)
- F04B 19/24 (2006.01)
- F04B 17/00 (2006.01)
- F04B 37/02 (2006.01)
- B05B 1/08 (2006.01)
- B05B 1/14 (2006.01)
- E01B 5/18 (2006.01)

(52) U.S. Cl. ............... 422/305; 422/1; 422/5; 422/119; 422/123; 422/124; 422/125; 422/257; 422/307; 417/207; 417/208; 417/413.2; 417/51; 239/101; 239/136; 239/102.2; 239/589.1; 239/590.3; 239/23; 239/695; 239/708

(58) Field of Classification Search ............. 239/102.2, 239/101, 136, 589.1, 590.3, 23, 695, 708; 417/207–208, 413.2, 51; 422/1, 5, 119, 123–125, 422/257, 305, 307

See application file for complete search history.

(56) References Cited

U.S. PATENT DOCUMENTS

| | | | | |
|---|---|---|---|---|
| 3,900,162 A | * | 8/1975 | Titus et al. | 239/102.2 |
| 4,370,300 A | * | 1/1983 | Mori et al. | 422/108 |
| 5,224,651 A | * | 7/1993 | Stahl | 239/77 |
| 5,518,179 A | * | 5/1996 | Humberstone et al. | 239/102.2 |
| 6,116,517 A | * | 9/2000 | Heinzl et al. | 239/101 |
| 6,175,772 B1 | * | 1/2001 | Kamiya et al. | 700/31 |
| 6,422,823 B2 | * | 7/2002 | Bernard et al. | 417/18 |
| 6,470,904 B1 | * | 10/2002 | Tai et al. | 137/15.18 |
| 6,520,753 B1 | * | 2/2003 | Grosjean et al. | 417/379 |

FOREIGN PATENT DOCUMENTS

DE 10027428 A1 * 12/2001

OTHER PUBLICATIONS

English translation of DE 10027428 A1.*

* cited by examiner

*Primary Examiner*—Jill Warden
*Assistant Examiner*—Monzer R Chorbaji
(74) *Attorney, Agent, or Firm*—Pro-Techtor Int'l Services

(57) ABSTRACT

A controlled odor generator, comprising a central processing unit, at least one micropump unit, a sensor unit and a fan. The micropump unit is housed in a casing containing odorous fluid and has a micropump array for ejecting the odorous fluid in tiny droplets. The central processing unit regulates operation of the micropump unit, allowing to control timing quantity and mixture of spread odor. The sensor unit provides the central processing unit with environmental data, like temperature, air density and humidity, as well as human body states for controlling the micropump unit. Environmental changes are followed by a change of spraying of odor, and varying taste and demand are adapted to.

12 Claims, 6 Drawing Sheets

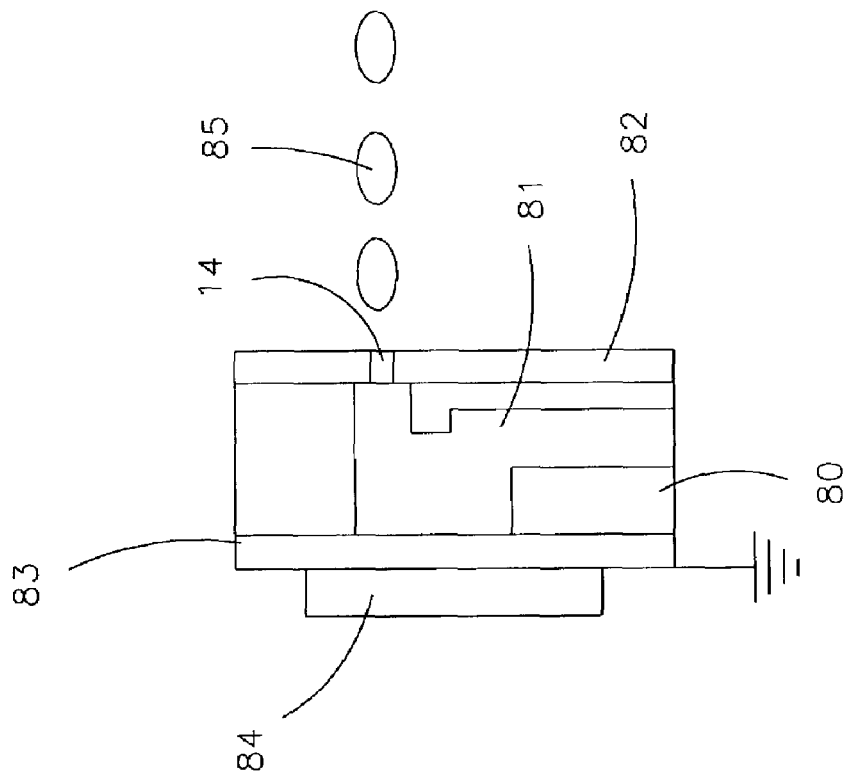
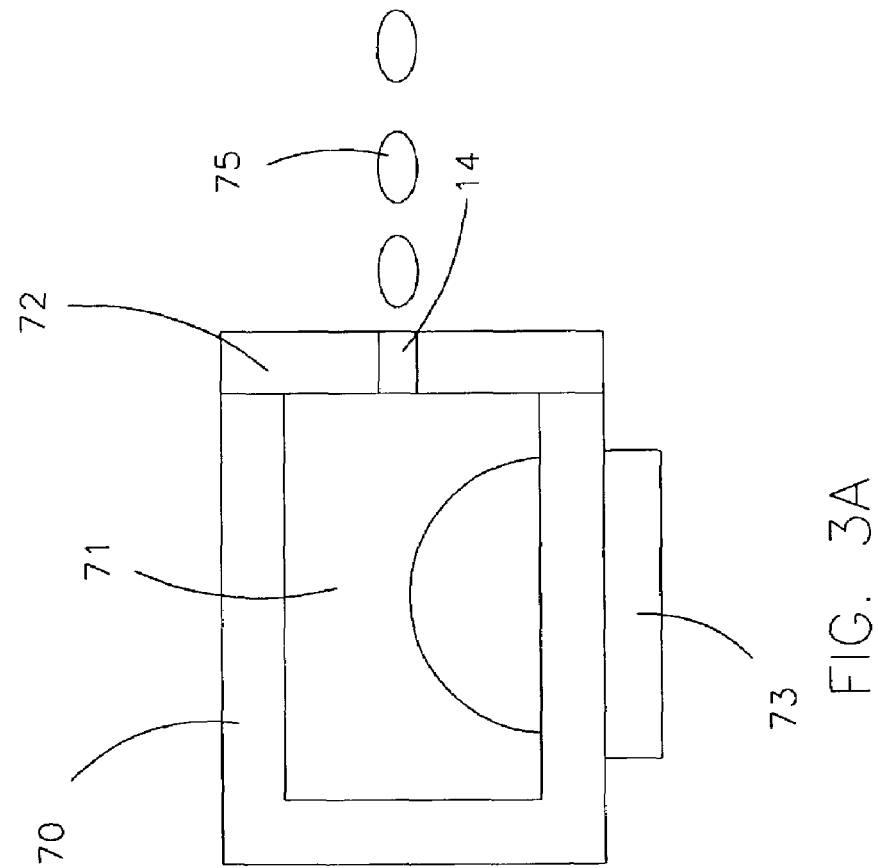
FIG. 3B
FIG. 3A

CONTROLLED ODOR GENERATOR

BACKGROUND OF THE INVENTION

1. Field of the Invention

The present invention relates to a controlled odor generator, particularly to a controlled odor generator having a micropump for creating and mixing suitable odors according to any setting or environment.

2. Description of Related Art

With quality of life on the increase, more and more techniques are applied to control and improve the environment. Conventionally, environment control is performed with respect to lighting and temperature. Research, however, has identified odor as an important factor influencing human well-being, therefore in recent years efforts have been started to use odors to affect living conditions.

Conventional devices for generating odor mainly use an odorous substance which is passively spread in the surrounding air either freely or along with vapor. However, a passive spreading method does not allow for controlling density or distribution of the odorous substance in the surrounding air, and there is no way to respond to changing environmental conditions. Thus the odorous substance is often wasted and is applicable in closed rooms only.

Another type of conventional odor generator uses a sprinkling device in conjunction with a timer for spreading a certain quantity of an odorous substance in the surrounding air during a certain time span. This is performed by mechanical ejecting of droplets using gas pressure. However, this method leads to droplets which, being too large and nonuniform, are not evenly dispersed in the surrounding air and are therefore used inefficiently. Control of spreading of the odorous substance is limited to total quantity and time, as well, restricting possible applications.

SUMMARY OF THE INVENTION

The present invention has a sprayer driven by a micropump array element which is controlled by a central processing unit connected with a sensor. By sensing and processing environmental data, like temperature, air density and humidity, the micropump array element is controlled to eject droplets at suitable time intervals in a suitable quantity for generating a certain odor. Then a microfan or external ventilation spreads the odor. Alternatively, the central processing unit is manually controlled to generate odor. The micropump array element of the controlled odor generator of the present invention is manufactured using a micromechanical process, sometimes referred to as microelectromechanical systems (MEMS), and has small dimensions (on the scale of microns to millimeters) and is suitable for mass production, thus being usable in personal devices generating large varieties of odor.

The present invention receives signals from an external sensor representing environmental conditions. The signals are processed in the processing unit for controlling timing and quantity of ejecting odorous fluid. Environmental changes are followed by a change of spraying. Several micropumps ejecting different odorous substances are combinable, with ejected quantities thereof being variable to generate a large range of odors.

An example of application of the present invention is generating odor inside a car. Driving parameters, atmospheric data from the interior of the car and the state of the driver are monitored, and a refreshing odor is issued at a suitable time to activate the driver and passengers, or, if an abnormal state of the driver is detected, a stimulating odor is generated to alert the driver and maintain safety.

In another embodiment, the present invention is used in conjunction with entertainment equipment, like stereo and video devices, to enhance lively experience by odor.

In yet another embodiment, the present invention is portable and used in conjunction with medical equipment, having a disposable sprayer allowing a patient to inhale medicine.

The present invention can be more fully understood by reference to the following description and accompanying drawings.

BRIEF DESCRIPTION OF THE DRAWINGS

FIG. 3A is a schematic illustration of a conventional thermal bubble micropump.

FIG. 3B is a schematic illustration of a conventional piezoelectric micropump.

DETAILED DESCRIPTION OF THE PREFERRED EMBODIMENTS

Figure 1:
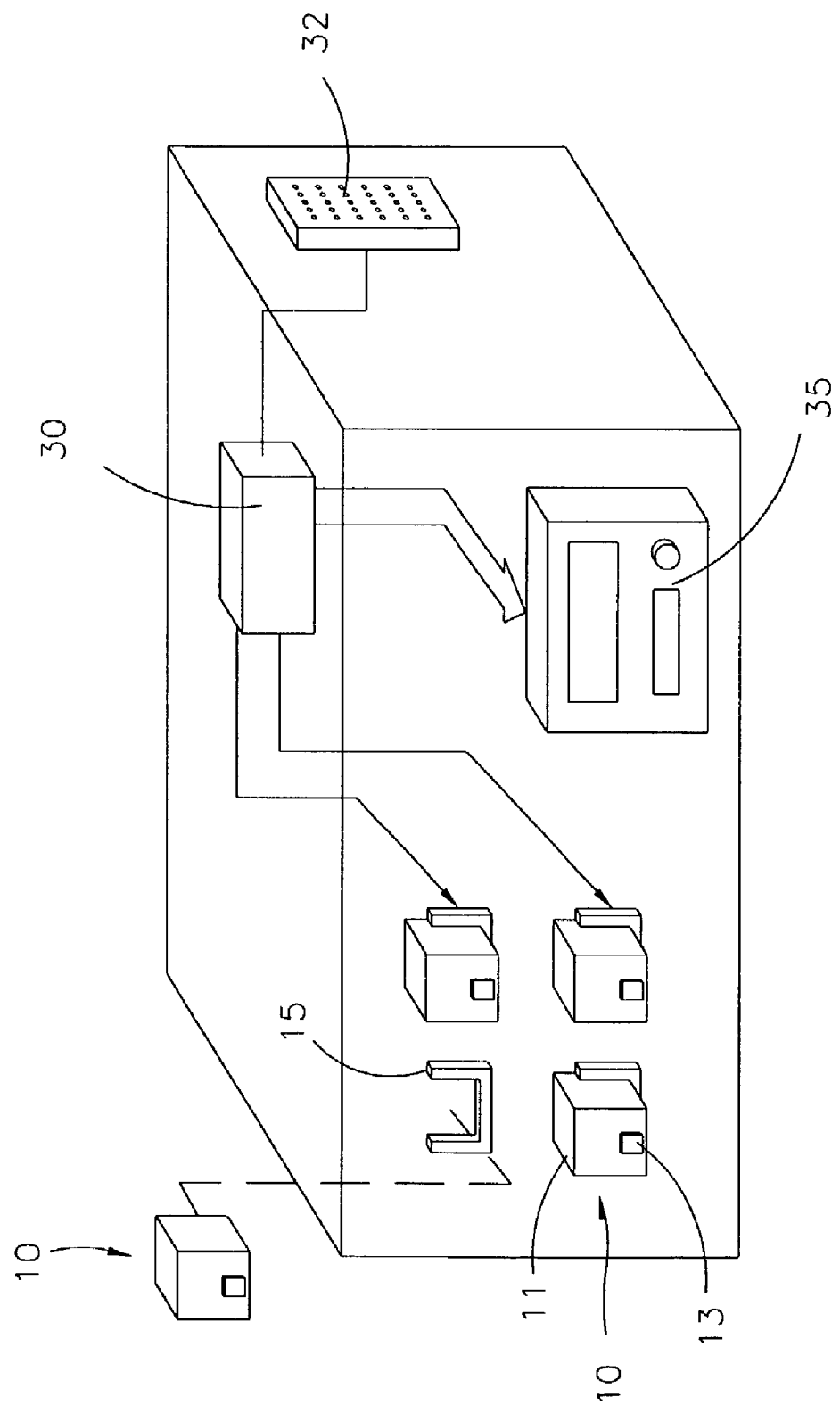
FIG. 1 is a schematic perspective view of the controlled odor generator of the present invention in the first embodiment.

As shown in FIG. 1, the controlled odor generator of the present invention mainly comprises: at least one micropump unit 10; a central processing unit 30 for controlling the micropump units 10, having a connector 32 for receiving signals; and a control panel 35, allowing manual setting of signals.

Figure 2A:
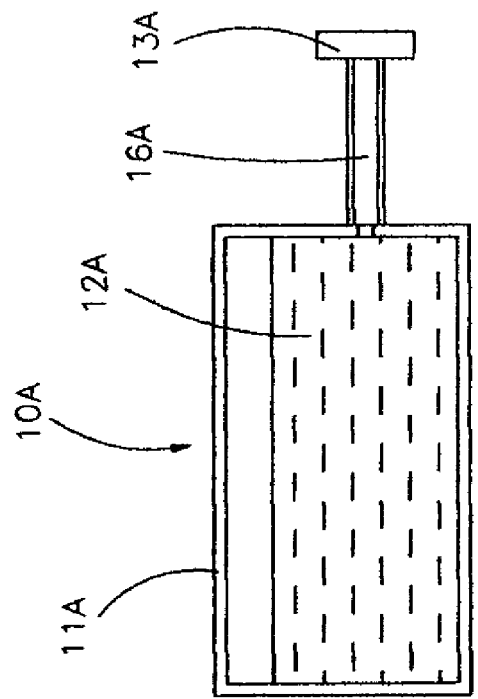
FIGS. 2 and 2A are schematic illustrations of the micropump of the present invention.
Figure 2:
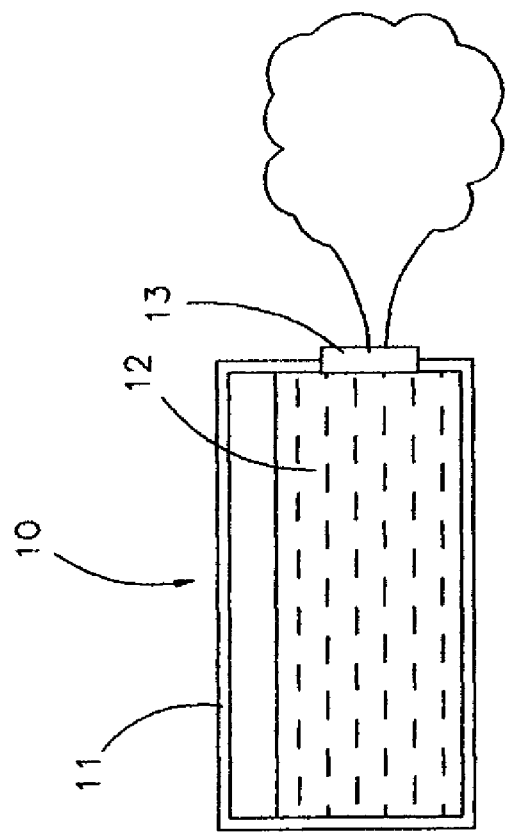

As shown in FIG. 2, each of the micropump units 10 comprises: a casing 11, filled with odorous fluid 12; a base 15, on which the casing 11 is set, so that the casing 11 is replaceable; and a micropump array 13, vaporizing and ejecting the odorous fluid 12 by micropulsation, thus generating odor in the environment.

In the embodiment of the present invention shown in FIG. 2, the micropump array element 13 is integral with the casing 11 and is thus replaced along with the casing 11. Another embodiment of the present invention, shown in FIG. 2A, has a micropump unit 10A with a casing 11A and a micropump array element 13A which are separated, being connected by a tube 16A.

Figure 3C:
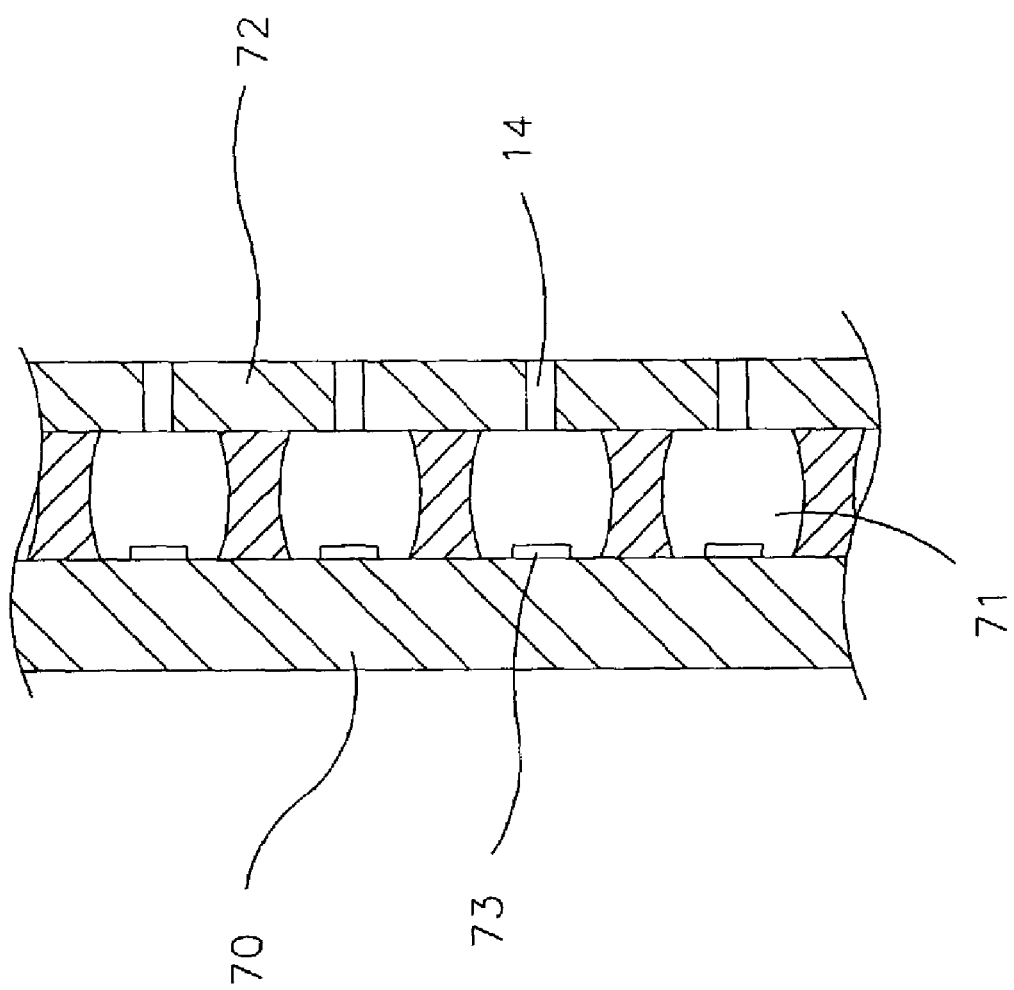
FIG. 3C is a sectional view of the micropump of the present invention, taken along line 3C-3C in FIG. 3.
Figure 3:
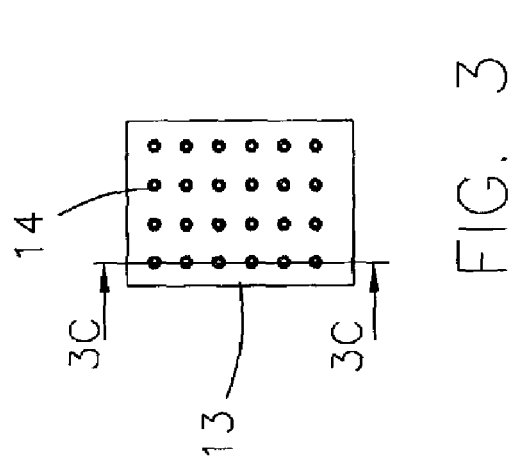
FIG. 3 is a front view of the micropump of the present invention.

Referring to FIG. 3, the micropump array element 13 is manufactured using a micro- fabrication process, having a plurality of elements arranged in rows, with corresponding nozzles 14, so that tiny droplets are ejected. Thus the odorous fluid 12 is ejected as fine vapor and evenly distributed in the surrounding air. As shown in FIGS. 3A and 3B, the micropump array element 13 is a thermal bubble micropump or a piezoelectric micropump.

Referring to FIG. 3C, a thermal bubble micropump, which operates conventionally, has a multi-layer structure with substrate layer 70, enclosing one pump chamber 71 or a plurality of pump chambers 71, a heating plate layer 73 formed on an interior wall of each pump chamber 71 and a conduit (not shown), allowing odorous fluid to enter the pump chambers 71. Furthermore, a nozzle plate 72 is glued to the substrate layer 70 having a plurality of nozzles 14, with each nozzle 14 being connected with one of the pump chambers 71. The micro-fabricated multi-layer assembly including the substrate layer 70, the pump chambers 71, the heating plates 73, and the nozzle plate 72 constitutes a thermal bubble micropump array element 13, which is positioned for fluid communication with the odorous fluid in the casing. When odorous fluid enters the pump chambers 71, intermittent heating of the heating plate 73 vaporizes the odorous fluid, causing tiny droplets 75 thereof to be ejected through the nozzles 14, so that odor is spread in the surrounding air environment which is suitable for human occupation.

Referring again to the schematic illustration of a conventional piezoelectric pump of FIG. 3B, a piezoelectric micropump of a piezoelectric micropump array element 13 of the instant invention has a multi-layer structure with a substrate layer 80, enclosing a pump chamber 81 which is covered by a nozzle plate 82. The nozzle plate 82 has a nozzle 14. A vibrating plate layer 83 is placed opposite to the nozzle plate 82, with a piezoelectric plate 84 being attached to a surface of the vibrating plate layer 83 exterior of the pump chamber 81. The micromechanical-fabricated multi-layer assembly including the substrate layer 80, the pump chambers 81, the vibrating plate layer 83, and the nozzle plate 82 constitutes a piezoelectric micropump array element 13, which is positioned for fluid communication with the odorous fluid in the casing. Vibrations of the vibrating plate cause tiny droplets 85 of an odorous fluid in the pump chamber 81 to be ejected through the nozzle 14.

The micropump units 10 of the present invention effectively generate vapor in tiny droplets at preset times and quantities, readily responding to control signals from the central processing unit 30. Thus odor is generated in predefined time intervals, quantities and mixture.

Figure 4:
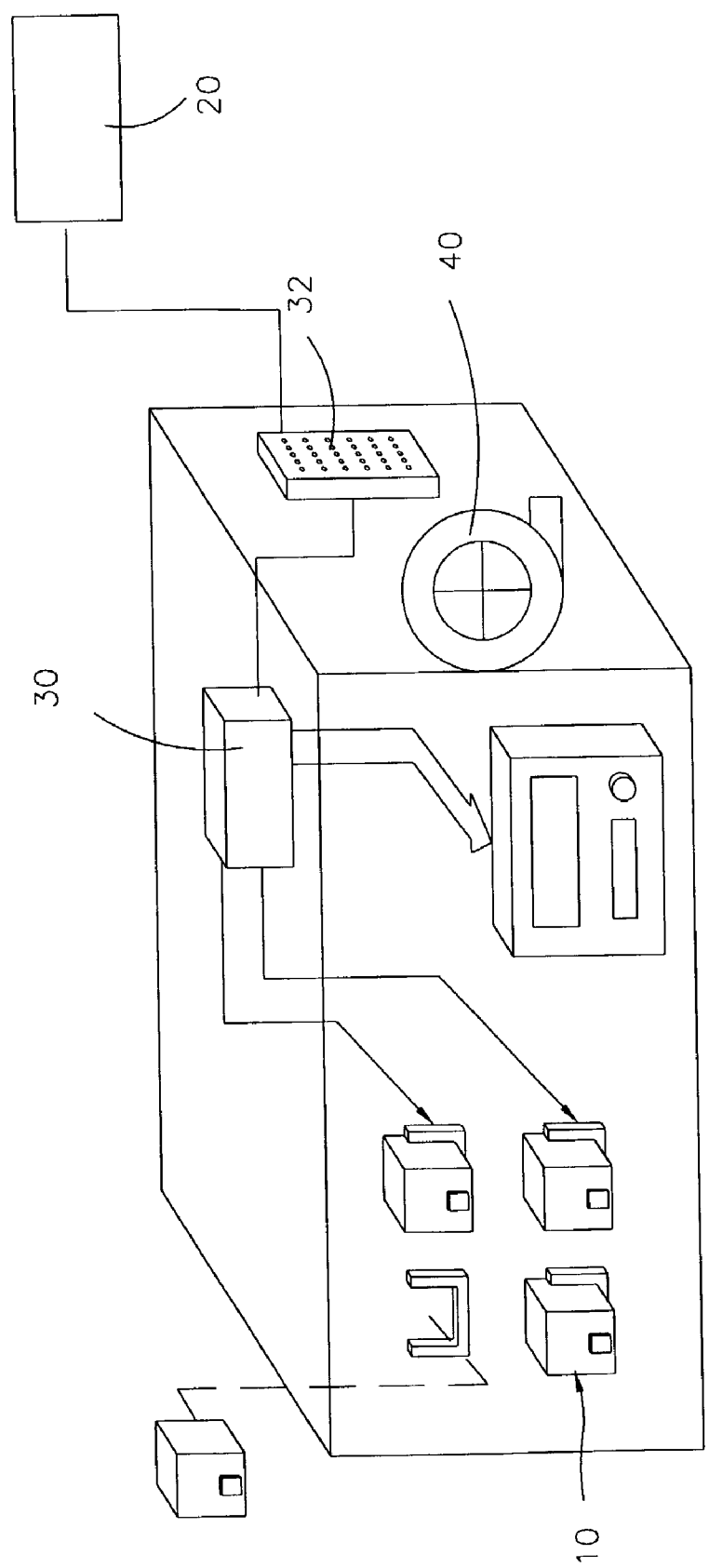
FIG. 4 is a schematic perspective view of the controlled odor generator of the present invention in the second embodiment.
Figure 5:
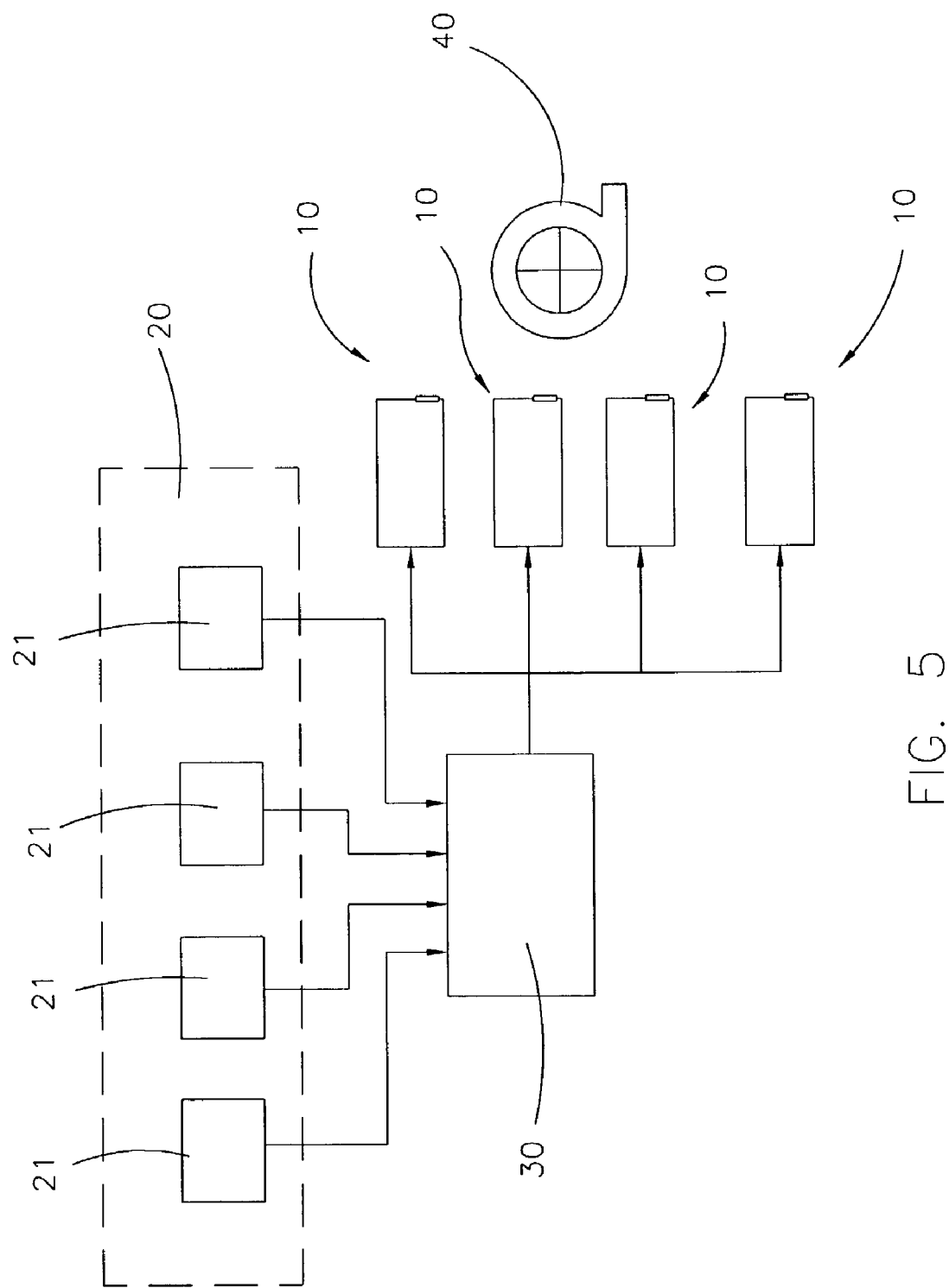
FIG. 5 is a schematic diagram of the controlled odor generator of the present invention in the second embodiment.

As shown in FIGS. 4 and 5, the present invention in a second embodiment additionally has a sensor unit 20 with built-in sensors 21, connected with the connector 32. The sensors 21 measure environmental parameters, like temperature, humidity, human states, lighting and air composition, which are transmitted to the central processing unit 30. The central processing unit 30 generates control signals based on the sensed environmental parameters controlling the micropump units 10, so that generated odor responds to environmental conditions. A fan 40 spreads odorous fluid 12 in the surrounding air.

For operating the controlled odor generator of the present invention, each micropump unit 10 is filled with a certain kind of odorous fluid 12. Separate control of each micropump unit 10 by the central processing unit 30 allows to mix various odors, which are effectively spread by the fan 40, creating a range of well-defined odors.

The present invention, by employing micropump units, a sensor unit and a central processing unit, generates odors for persons in various states and under varying conditions in a closed space, precisely controlling quantity and flavor. Thus, responding to environmental change, well-being of persons is enhanced, and a healthy effect is achieved. Furthermore, by using the present invention in conjunction with equipment for visual and acoustic effects, lively scent is added to a sensual experience.

While the invention has been described with reference to preferred embodiments thereof, it is to be understood that modifications or variations may be easily made without departing from the spirit of this invention which is defined by the appended claims.

The invention claimed is:

1. A controlled odor generator, comprising:
a central processing unit; and
at least one micropump unit, each having
  a casing filled with odorous fluid,
  at least one micropump array element, each being a unitized array of micropumps, having electrical communication with said central processing unit and fluidic communication with said casing, each said micropump array element further comprising
    a substrate layer,
    a nozzle plate having a plurality of nozzles, and
    a plurality of separate pump chambers formed between said substrate layer and said nozzle plate, each said pump chamber configured to fluidly communicate with at least one nozzle of said nozzle plate, each said pump chamber having a separate excitation plate having electrical communication with said central processing unit;
a fan for evenly distributing odorous fluid ejected by said at least one micropump unit; and
a sensor unit having at least one sensor located in an environment suitable for human occupation;
wherein said central processing unit controls said at least one micropump array element pumping a fluid, in tiny droplets into said environment suitable for human occupation, thereby changing odor in the surrounding air, and
wherein for each of said at least one micropump units said casing is detachable from a base for easy replacement; and
wherein each micropump in said at least one micropump array element is a piezoelectric micropump, with each pump chamber thereof being defined by said nozzle plate on one side and a vibrating plate on an opposing side, with a piezoelectric plate attached to an exterior surface of said vibrating plate opposite said pump chamber;
whereby energizing said piezoelectric plate causes the vibrating plate to vibrate, thereby causing droplets of odorous fluid to be ejected through at least one of said nozzles.

2. A controlled odor generator according to claim 1, wherein a plurality of micropump units eject a plurality of odorous fluids of various kinds under the control of said central processing unit.

3. A controlled odor generator according to claim 1, wherein for each of said at least one micropump units said micropump array element is mounted directly on a wall of said casing.

4. A controlled odor generator according to claim 1, wherein for each of said at least one micropump units said casing is separate from said micropump array element, being connected by a tube to said micropump array element.

5. A controlled odor generator according to claim 1, wherein said central processing unit controls time cycles, quantities and mixtures of odorous fluid to generate odors according to individual taste and demand.

6. A controlled odor generator according to claim 1, used in conjunction with equipment for visual and acoustic effects for additionally generating odor.

7. A controlled odor generator according to claim 1, used in conjunction with medical equipment, allowing a patient to inhale medicine at well-defined times.

8. A controlled odor generator according to claim 1, wherein said central processing unit is connected with a control panel.

9. A controlled odor generator, comprising:

a central processing unit; and at least one micropump unit, each having a casing filled with odorous fluid, at least one micro-fabricated micropump array element, each being a unitized array of micropumps, having electrical communication with said central processing unit and fluidic communication with said casing, each said micropump array element further comprising a substrate layer, a nozzle plate having a plurality of nozzles, and a plurality of separate pump chambers formed between said substrate layer and, said nozzle plate, each said pump chamber configured to fluidly communicate with at least one nozzle of said nozzle plate, each said pump chamber having a separate excitation plate having electrical communication with said central processing unit;

wherein said, central processing unit controls said at least one micropump array element pumping a fluid in tiny droplets, thereby changing odor in the surrounding air wherein each micropump in said at least one micro-fabricated micropump array element is a piezoelectric micropump, with each pump chamber thereof being defined by said nozzle plate on one side and a vibrating plate on an opposing side, with a piezoelectric plate attached to a surface of said vibrating plate opposite to and exterior of said pump chamber;

whereby energizing said piezoelectric plate causes the vibrating plate to vibrate, thereby causing droplets of odorous fluid to be ejected through at least one of said nozzles.

10. A controlled odor generator according to claim 9, wherein each micropump unit further comprises a fan for evenly distributing odorous fluid ejected by said at least one micropump unit; and a sensor unit having at least one sensor located in an environment suitable for human occupation;

wherein said central processing unit controls said at least one micropump array element pumping a fluid in tiny droplets into said environment suitable for human occupation, thereby changing odor in the surrounding air, and wherein for each of said at least one micropump units said casing is detachable from a base for easy replacement.

11. A controlled odor generator according to claim 9, wherein for each of said at least one micropump units said casing is detachable from a base for easy replacement.

12. A controlled odor generator according to claim 9, wherein each micropump in said at least one micro-fabricated micropump array element is a thermo bubble micropump with each pump chamber thereof enclosing a separate heating plate;

whereby heating of said heating plate causes droplets of odorous fluid to be ejected through at least one of said nozzles.

* * * * *